(12) United States Patent
Beech, Jr. et al.

(10) Patent No.: US 7,906,697 B2
(45) Date of Patent: Mar. 15, 2011

(54) METHOD OF CIRCULATING CATALYST BETWEEN A CATALYST REGENERATOR AND AN EXTERNAL CATALYST COOLER

(75) Inventors: James H. Beech, Jr., Kingwood, TX (US); Chunshe Cao, Houston, TX (US); Michael P. Nicoletti, Houston, TX (US); James R. Lattner, LaPorte, TX (US); Jesse F. Goellner, Pittsburgh, PA (US); Rutton D. Patel, Arlington, VA (US); Timothy M. Healy, Centreville, VA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 461 days.

(21) Appl. No.: 12/059,717

(22) Filed: Mar. 31, 2008

(65) Prior Publication Data

US 2009/0192341 A1 Jul. 30, 2009

Related U.S. Application Data

(60) Provisional application No. 61/024,805, filed on Jan. 30, 2008.

(51) Int. Cl.
*C07C 2/04* (2006.01)
(52) U.S. Cl. ........ 585/520; 585/638; 585/639; 585/640; 502/38; 502/41; 423/210; 422/212; 23/313 FB
(58) Field of Classification Search .................. 585/520, 585/638, 639, 640; 502/38, 41; 423/210; 422/212; 23/313 FB
See application file for complete search history.

(56) References Cited

U.S. PATENT DOCUMENTS

| 2,394,710 | A | | 2/1946 | McAfee |
| 4,071,573 | A | | 1/1978 | Owen et al. |
| 4,678,836 | A | * | 7/1987 | McKinney et al. ............ 525/221 |
| 2006/0135348 | A1 | | 6/2006 | Cunningham et al. |
| 2006/0135358 | A1 | | 6/2006 | Lattner et al. |
| 2006/0135836 | A1 | * | 6/2006 | Beech et al. .................. 585/640 |
| 2006/0149108 | A1 | | 7/2006 | Miller |
| 2007/0142212 | A1 | | 6/2007 | Pujado |
| 2007/0232844 | A1 | | 10/2007 | Kuechler et al. |

FOREIGN PATENT DOCUMENTS

EP 0 330 304 8/1989

* cited by examiner

*Primary Examiner* — Prem C Singh
(74) *Attorney, Agent, or Firm* — Kevin M. Faulkner; David M. Weisberg (57) ABSTRACT

This invention relates to efficiently regenerating catalyst particles by minimizing the formation of localized "hot spots" and "cold spots" in a regeneration zone. Specifically this invention relates to a method for controlling regenerator temperature in an oxygenates-to-olefins system, comprising the steps of: contacting an oxygenate feed in a reactor with a catalytically effective amount of molecular sieve-containing catalyst under conditions effective for converting said oxygenate to a product containing light olefins and forming a coked catalyst; contacting a portion of the coked catalyst in a regenerator, having a catalyst bed height ($H_c$), an inlet height ($H_i$), and an outlet height ($H_o$), with an oxygen-containing regeneration medium under conditions effective to at least partially regenerate the coked catalyst; and conducting a portion of the catalyst from the regenerator to a catalyst cooler to form a cooled catalyst portion, wherein $H_o$ is greater than $H_i$.

20 Claims, 5 Drawing Sheets

METHOD OF CIRCULATING CATALYST BETWEEN A CATALYST REGENERATOR AND AN EXTERNAL CATALYST COOLER

CROSS-REFERENCE OF RELATED APPLICATIONS

This application claims priority to and the benefit of U.S. Provisional Application No. 61/024,805, filed Jan. 30, 2008.

FIELD OF THE INVENTION

The present invention relates to regenerating catalyst. More particularly, the invention relates to controlling catalyst temperature during the regeneration process.

BACKGROUND OF THE INVENTION

Light or prime olefins, defined herein as ethylene and propylene, serve as feeds for the production of numerous chemicals. Olefins traditionally are produced by petroleum cracking. Because of the limited supply and/or the high cost of petroleum sources, the cost of producing olefins from petroleum sources has increased steadily.

Alternative feedstocks for the production of light olefins are oxygenates, such as alcohols, particularly methanol, dimethyl ether, and ethanol. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

The conversion of oxygenates to olefins (OTO), particularly the conversion of methanol to olefins (MTO), in a hydrocarbon conversion apparatus generates and deposits carbonaceous material (coke) on the molecular sieve catalysts used to catalyze the conversion process. Excessive accumulation of these carbonaceous deposits will interfere with the catalyst's ability to promote the reaction. In order to avoid unwanted build-up of coke on molecular sieve catalysts, the OTO and MTO processes incorporate a second step comprising catalyst regeneration. During regeneration, the coke is at least partially removed from the catalyst by combustion with oxygen, which restores the catalytic activity of the catalyst and forms a regenerated catalyst. The regenerated catalyst then may be reused to catalyze the conversion of methanol to olefins.

The combustion of the carbonaceous deposits from molecular sieve catalyst compositions during catalyst regeneration is an exothermic process. The exothermic nature of catalyst regeneration presents a problem in OTO regeneration systems because the amount of coke formed on the molecular sieve catalyst compositions utilized in OTO reaction systems preferably is maintained at higher levels in order to maintain a high prime olefin (ethylene and propylene) selectivity. As a result, the amount of heat liberated from the OTO molecular sieve catalyst compositions during catalyst regeneration is significantly great.

The tremendous amount of heat liberated during the regeneration of heavily coked catalyst particles, such as coked OTO catalyst particles, may exceed the metal tolerances of the metals used to form the catalyst regenerator, particularly of the separation vessels, e.g., cyclone separators, contained therein as well as the conduits used to transport regenerated catalyst back to the hydrocarbon conversion apparatus. The creation of localized "hot spots" in catalyst regenerators also poses a significant problem in that catalyst is not regenerated uniformly throughout the regeneration zone. The heat also can damage and/or deactivate the catalyst particles themselves.

U.S. Publication No. 2006-0135348 A1, filed Mar. 2, 2005, discloses a regeneration system and a process for regenerating catalyst. The invention relates to efficiently regenerating catalyst particles by minimizing the formation of localized "hot spots" and "cold spots" in a regeneration zone. The document discloses that the invention includes mixing spent catalyst from a reactor and cold catalyst from a catalyst cooler and directing the mixed catalyst to the regeneration zone in a fluidized manner with a fluidizing medium. In the regeneration zone, the mixed catalyst contacts an oxygen-containing regeneration medium under conditions effective to regenerate the spent catalyst contained therein.

U.S. Patent Application Publication No. 2006/0149108 discloses a process of converting oxygenates to olefins wherein a catalyst cooler is attached to the reactor to cool the spent catalyst before it is reintroduced to fresh oxygenate feedstream. The publication discloses withdrawing all of the spent catalyst that enters the catalyst cooler from the bottom of the catalyst cooler. The publication also disclosures a catalyst cooler with a plurality of cooling tubes, a fluidizing gas distributor and a catalyst inlet above the catalyst outlet, the outlet being located at the bottom of the catalyst cooler.

It would also be desirable to reduce the catalyst hold-up in this OTO system. This would result in a reduction in the total amount of expensive catalyst required in the system as well as reducing the time in which the catalyst is exposed to deactivating conditions in the regenerator.

Improved processes are sought for regenerating highly coked catalyst particles, such as coked catalyst particles derived from OTO reaction systems, while maintaining desirable temperature characteristics in the OTO catalyst regenerator through improved mixing of the catalyst and higher catalyst circulation rates between the regenerator and the catalyst cooler. In particular there is a need to reduce/minimize the amount of catalyst in the OTO reaction system, e.g., by decreasing the amount of catalyst that is held up in the system.

BRIEF DESCRIPTION OF THE DRAWINGS

This invention will be better understood by reference to the Detailed Description of the Invention when taken together with the attached Drawings, wherein:

FIGS. 5a-5e illustrate cross-sectional views of different embodiments of the design of regenerator systems according to the invention; FIG. 5a corresponds roughly to the arrangement shown in perspective view in FIG. 4. In these Figures, white shapes represent catalyst cooler inlets, black shapes represent catalyst cooler outlets, and gray shapes represent inlets and outlets for inert circulation not associated with a catalyst cooler. In addition, in these Figures, circular geometries indicate flow out of the plane of the paper, and rectangular geometries indicate flow within the plane of the paper along the direction of the longer parallel sides.

SUMMARY OF THE INVENTION

One aspect of the invention relates to an MTO regenerator system having a (1) regenerator vessel, containing a bed of MTO catalyst and an oxygen-containing regeneration medium, the vessel having a catalyst circulation rate and a regenerator efficiency, the bed having a top and a bottom, (2) a catalyst cooler containing a catalyst cooler medium, (3) a first conduit means for conducting MTO catalyst from the regenerator vessel to the catalyst cooler, and (4) a second conduit means for conducting cooled MTO catalyst from the catalyst cooler to the regenerator vessel; wherein the first conduit means comprises a collection zone located in the catalyst bed at a height, $H_1$, from the bottom of the catalyst bed, and wherein the second conduit means conducts the cooled MTO catalyst to an inlet located at a height, $H_2$, above the bottom of the catalyst bed; the improvement comprising substituting the first conduit means with a third conduit means comprising an outlet from the regenerator vessel located at a height, $H_3$, from the bottom of the catalyst bed; and substituting the second conduit means with a fourth conduit means comprising an inlet to the regenerator vessel located at a height, $H_4$, which is greater than $H_1$, $H_2$, and $H_3$; in order to increase the catalyst circulation rate, and the mixing of the catalyst in the catalyst bed, so as to increase the overall regenerator efficiency.

Another aspect of the invention relates to a method for controlling regenerator temperature in an oxygenates-to-olefins system, comprising the steps of: (1) contacting a feed comprising an oxygenate in a reaction zone of a reactor with a catalytically effective amount of molecular sieve-containing catalyst in a reactor under conditions effective for converting said oxygenate to a product containing light olefins, and forming a coked catalyst; (2) conducting a portion of the at least partially coked catalyst from the reaction zone to a regenerator having a catalyst bed, a catalyst cooler, a catalyst cooler inlet, a catalyst cooler outlet, a catalyst bed height ($H_c$), an catalyst cooler inlet height ($H_i$), and a catalyst cooler outlet height ($H_o$); (3) contacting a portion of the coked catalyst in a regeneration zone of the regenerator with an oxygen-containing regeneration medium at a first temperature, under conditions effective to at least partially regenerate the coked catalyst; and (4) conducting a portion of the catalyst from the regenerator through the catalyst cooler inlet to the catalyst cooler to form a cooled portion of catalyst, which is then conducted through the catalyst cooler outlet back into the regenerator to control temperature in the regenerator, wherein $H_o$ is greater than $H_i$.

Another aspect of the invention relates to a method for controlling regenerator temperature in an oxygenates-to-olefins system, comprising the steps of: (a) contacting a feed comprising an oxygenate with a catalytically effective amount of a molecular sieve-containing catalyst in a reaction zone under conditions sufficient to convert said oxygenate to a product containing light olefins, and thereby forming an at least partially coked catalyst; (b) conducting a portion of the at least partially coked catalyst from the reaction zone to a regenerator having a regenerator height ($H_r$), a catalyst bed, a catalyst bed height ($H_c$), at least two catalyst cooler inlets, and at least two catalyst cooler outlets; (c) contacting a portion of the at least partially coked catalyst in the regenerator with an oxygen-containing regeneration medium at a first temperature, under conditions effective to at least partially regenerate the at least partially coked catalyst; and (d) conducting a portion of the catalyst from the regenerator through one or more of the at least two catalyst cooler inlets to the catalyst cooler to form a cooled portion of catalyst, which is then conducted through one or more of the at least two catalyst cooler outlets back into the regenerator to control temperature in the regenerator, wherein: (i) each inlet and outlet has a center; (ii) two or more of the at least two outlet centers and the at least two cooler inlet centers define a line; (iii) two or more of the at least two cooler inlet centers and the regenerator height form one or more inlet planes; (iv) two or more of the at least two cooler outlet centers and the regenerator height define one or more outlet planes; and (v) at least one of the one or more inlet planes and at least one of the one or more outlet planes are substantially not coplanar. In one embodiment of this aspect of the invention, the at least two cooler inlets can be positioned at first positions along the regenerator height at a common inlet height ($H_i$), the at least two cooler outlets can be positioned at second positions along the regenerator height at a common outlet height ($H_o$), and the at least two first positions can be above the at least two second positions such that $H_i$ is greater than $H_o$. In another embodiment of this aspect of the invention, the at least two cooler inlets can be positioned at first positions along the regenerator height at a common inlet height ($H_i$), the at least two cooler outlets can be positioned at second positions along the regenerator height at a common outlet height ($H_o$), and the at least two first positions can be below the at least two second positions such that $H_o$ is greater than $H_i$.

Each of the heights disclosed herein (e.g., $H_1$, $H_2$, $H_3$, $H_4$, $H_c$, $H_o$, $H_i$, and $H_r$) should be understood to be measured from a common base at the bottom of the regenerator catalyst bed.

DETAILED DESCRIPTION OF THE EMBODIMENTS

In an embodiment, the invention is directed to controlling the temperature of catalyst regeneration, preferably in an OTO reaction process. Specifically, this invention is directed toward a regeneration system which comprises a regenerator and a catalyst cooler.

It has been discovered that that achieving a high catalyst circulation rate between the regenerator and the catalyst cooler, leading to low catalyst ΔT, results in an improved OTO reaction process, as described in more detail herein. Catalyst ΔT is defined as the temperature at the catalyst cooler inlet minus the temperature at the catalyst cooler outlet. Overall good mixing of the cooled catalyst, and minimizing cold and hot spots, also can result in an improved process.

It has also been discovered that the method of circulating the catalyst can greatly influence the rate at which catalyst can be circulated and affect the efficiency of catalyst regeneration and potential catalyst deactivation. This invention describes a preferred method of circulating catalyst between an MTO regenerator and its external catalyst cooler.

Additionally, it has been discovered that efficiently regenerating catalyst particles by minimizing the formation of localized "hot spots" and "cold spots" in the regenerator also results in an improved process, as described herein. This minimization may be accomplished with thorough mixing of the cooled catalyst when it is returned to the regenerator to maintain a uniform regenerator temperature and keep burning efficiency high.

Oxygenate to Olefin Reaction Systems

In an embodiment, the invention is directed to controlling the temperature of catalyst regeneration, preferably in an OTO reaction process. The first step in an OTO reaction process involves contacting a feed comprising an oxygenate in a reaction zone of a reactor with a molecular sieve-containing catalyst in a reaction zone under conditions effective for converting said oxygenate to a product containing light olefins, and forming a coked catalyst. In conventional regeneration vessels, coked catalyst is directed from the reactor to a catalyst regenerator. In a catalyst regenerator, a regeneration medium, usually oxygen, can enter the regenerator, and coke can be removed from the coked catalyst, e.g., by combustion with the regeneration medium, to form regenerated catalyst and gaseous byproducts. The bulk of the regenerated catalyst from the regenerator can then advantageously be returned to the reactor. The gaseous byproducts are typically forced out an exhaust outlet oriented in the upper section of the catalyst regenerator.

OTO reaction systems will now be described in greater detail. As used herein, "reaction system" means a system comprising a reactor, a catalyst cooler, optionally a catalyst regenerator, and optionally a catalyst stripper. The reactor comprises a reaction unit, which comprises a reaction zone, and optionally a disengaging unit, which comprises a disengaging zone.

Catalytic OTO reaction systems use a catalytically effective amount of a molecular sieve catalyst composition having catalytic activity for converting an oxygenate-containing feedstock to light olefins. In an embodiment, the molecular sieve catalyst composition comprises one or more inorganic oxides of silicon, aluminum, and phosphorus. In an embodiment, silicoaluminophosphate (SAPO) molecular sieve catalysts are used in the OTO process, because they have both (i) activity for olefin production and (ii) selectivity for the formation of ethylene and propylene. While catalysts containing SAPO molecular sieves are generally preferred, any fluidizable catalyst having catalytic activity for converting oxygenates to olefins can be used. Suitable SAPO molecular sieve catalyst compositions include, for example, SAPO-17, SAPO-18, SAPO-34, SAPO-35, SAPO-44, the substituted forms thereof, and mixtures thereof. The molecular sieve catalyst composition can contain a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof. Additionally or alternatively, the molecular sieve comprises an aluminophosphate (ALPO) molecular sieve. Preferred ALPO molecular sieves can include, but are not limited to, ALPO-5, ALPO-11, ALPO-18, ALPO-31, ALPO-34, ALPO-36, ALPO-37, ALPO-46, AEI/CHA intergrowths, mixtures thereof, and metal containing forms thereof. The catalyst can also contain one or more zeolites, such as, ZSM-34, ZSM-5, metal containing forms thereof, intergrown forms thereof, AEI/CHA zeolite intergrowths, and mixtures thereof.

In a preferred embodiment of the process of the invention, the feedstock contains one or more organic compounds containing at least one oxygen atom. In an embodiment, the oxygenate-containing feedstock used in the OTO reaction system can contain one or more aliphatic-containing compounds such as alcohols, amines, carbonyl compounds (for example, aldehydes, ketones, and carboxylic acids), ethers, halides, mercaptans, sulfides, and the like. The aliphatic moiety of the aliphatic-containing compounds typically contains from 1 to about 50 carbon atoms, preferably from 1 to 20 carbon atoms, more preferably from 1 to 10 carbon atoms, and even more preferably from 1 to 4 carbon atoms. A preferred feed contains methanol.

Suitable examples of aliphatic-containing compounds include, for example: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methyl ethyl ether, alkyl-halides such as methyl chloride and ethyl chloride, alkyl ketones such as dimethyl ketone, alkyl-aldehydes such as formaldehyde and acetaldehyde, and various acids such as acetic acid, inter alia.

The various feedstocks discussed above can be converted primarily into one or more olefins. The desired olefins produced from the feedstock typically have from 2 to 30 carbon atoms, preferably 2 to 8 carbon atoms, more preferably 2 to 6 carbon atoms, still more preferably 2 to 4 carbons atoms, and most preferably include ethylene and/or propylene.

Non-limiting examples of olefin monomers include, but are not limited to, ethylene, propylene, butene-1, pentene-1, 4-methyl-pentene-1, hexene-1, octene-1, decene-1, and mixtures thereof, preferably ethylene, propylene, butene-1, pentene-1,4-methyl-pentene-1, hexene-1, octene-1, isomers thereof, and mixtures thereof. Other olefin monomers can include, but are not limited to, unsaturated monomers, diolefins having 4 to 18 carbon atoms, conjugated or nonconjugated dienes, polyenes, vinyl monomers, cyclic olefins such as maleic anhydride, and mixtures thereof.

In a preferred embodiment, the feedstock, which ideally comprises methanol, can be converted in the presence of a molecular sieve catalyst composition into one or more olefins having 2 to 6 carbons atoms, preferably 2 to 4 carbon atoms. Most preferably, the one or more olefins, alone or combination, are converted from a feedstock containing an oxygenate, preferably an alcohol, most preferably containing methanol, to preferred olefins ethylene and/or propylene.

In an embodiment, the amount of liquid feedstock fed separately or jointly with a vapor feedstock to a reactor system can be in the range from 0.1 wt % to about 85 wt %, preferably from about 1 wt % to about 75 wt %, more preferably from about 5 wt % to about 65 wt %, based on the total weight of the feedstock, including any diluent contained therein. The liquid and vapor feedstocks are preferably the same composition, or contain varying proportions of the same or different feedstock with the same or different diluent.

The feedstock, in one embodiment, contains one or more diluents, typically used to reduce the concentration of the feedstock. The diluents are generally non-reactive to the feedstock or molecular sieve catalyst composition. Some examples of diluents include, but are not limited to, helium, argon, nitrogen, carbon monoxide, carbon dioxide, water, essentially non-reactive paraffins (especially alkanes such as methane, ethane, and propane), essentially non-reactive aromatic compounds, and mixtures thereof. Especially preferred diluents include water and nitrogen, with water being particularly preferred. In other embodiments, the feedstock may not contain any diluent.

The diluent may be used either in a liquid or a vapor form, or a combination thereof. The diluent can either be added directly to a feedstock entering into a reactor or added directly into a reactor, or be added with the molecular sieve catalyst composition. In one embodiment, the amount of diluent in the feedstock can be in the range from about 1 mol % to about 99 mol %, based on the total number of moles of the feedstock and diluent, preferably from about 1 mol % to 80 mol %, more preferably from about 5 mol % to about 50 mol %, most preferably from about 5 mol % to about 25 mol %. In one embodiment, other hydrocarbons can be added to the feedstock, either directly or indirectly, and can include, but may not necessarily be limited to, olefin(s), paraffin(s), aromatic(s) (see, for example, U.S. Pat. No. 4,677,242, addition of aromatics), or mixtures thereof, preferably propylene, butylene, pentylene, other hydrocarbons having 4 or more carbon atoms, or mixtures thereof.

In an embodiment, the OTO process can be a fixed bed process, a fluidized bed process (includes a turbulent bed process), preferably a continuous fluidized bed process, and more preferably a continuous, relatively high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types, for example, are described in U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all incorporated by reference in their entirety.

Suitable riser reactors are generally described in *Riser Reactor, Fluidization and Fluid-Particle Systems*, pages 48 to 59, F. A. Zenz and D. F. Othmer, Reinhold Publishing Corporation, New York, 1960; U.S. Pat. No. 6,166,282 (fast-fluidized bed reactor); and U.S. patent application Ser. No. 09/564,613, filed May 4, 2000 (multiple riser reactor), which are all incorporated by reference in their entirety.

The conversion temperature employed in the conversion process, specifically within the reaction zone of the reactor system, can be in the range from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) or from about 662° F. (350° C.) to about 1022° F. (550° C.).

The pressure employed in the conversion process, specifically within the different parts of the reactor system, can vary over a wide range including autogenous pressure. The conversion pressure is based on the partial pressure of the feedstock, exclusive of any diluent therein. Typically the conversion pressure employed in the process can be in the range from about 0.1 kPaa to about 5 MPaa, preferably from about 5 kPaa to about 1 MPaa, and more preferably from about 20 kPaa to about 500 kPaa.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), can be at least 0.1 meter per second (m/sec), preferably greater than 0.5 m/sec, more preferably greater than 1 m/sec, even more preferably greater than 2 m/sec, still more preferably greater than 3 m/sec, and even more preferably greater than 4 m/sec. See, for example, U.S. Ser. No. 09/708,753 filed Nov. 8, 2000, which is incorporated by reference in its entirety.

The processes and systems for controlling temperature in a catalyst regenerator according to the present invention will now be described in greater detail.

Processes for Controlling the Temperature During Catalyst Regeneration

During the catalytic conversion of hydrocarbons to various products, e.g., the catalytic conversion of oxygenates to light olefins (the OTO process), carbonaceous deposits accumulate on the catalyst. At some point, the build up of these carbonaceous deposits can cause a reduction in the capability of the catalyst to function efficiently, creating a spent or partially spent catalyst. For purposes of the present specification and appended claims, the term "spent catalyst" refers to a catalyst composition that has been at least partially deactivated (e.g., usually to a point where at least the activity of the spent catalyst is 50% or less of the activity of fresh or regenerated catalyst) by the accumulation of carbonaceous deposits. For example, in the OTO process, an excessively spent catalyst is less effective in converting the oxygenate feed to light olefins. When a catalyst can no longer convert the hydrocarbon to the desired product, the catalyst is considered to be fully spent.

Since the process of regenerating spent catalyst to form regenerated catalyst is typically an exothermic process, the temperature of the catalyst contained in regeneration zone typically increases—potentially exceeding the point at which the catalyst thermally decomposes, thereby causing catalyst deactivation. Therefore, it can be desirable to control the temperature of the catalyst within the regeneration system. This can be accomplished, for example, by maintaining temperatures relatively low (e.g., as low as possible) for efficient coke burning (approximately 1300° F. or about 700° C.), yet above the water critical point temperature (approximately 700° F. or about 370° C.). It can also by desirable to keep the temperatures within the regeneration system as uniform as possible, e.g., by minimizing the formation of "hot spots" and "cold spots." This may be accomplished by means of relatively high circulation rates among sections of the system and thorough mixing of the regeneration medium. As used herein, the term "hot spot" means any region where the local temperature is hot enough to damage the regenerator itself (e.g., the regenerator vessel or vessel and associated equipment which might be designed based on some average or normal range of regenerator temperatures). Also as used herein, the term "cold spot" means any region where the local temperature is significantly below the bulk average temperature, which may cause only partial burning of the coke or other hydrocarbons by the regeneration medium, which partial burning may thus produce excess quantities of carbon oxides, such as CO, which can then undergo more complete combustion, e.g., in the exhaust system of the regenerator, thereby also leading to equipment damage.

Specifically, the regeneration system temperature may be controlled by adjusting the temperature of the catalyst entering the regeneration system, for example, through the use of one or more catalyst coolers. When a catalyst cooler is used, relatively high catalyst circulation rates between the regenerator and the catalyst cooler can be advantageous to maintain a regenerator temperature from about 527° C. to about 760° C. Additionally, relatively thorough mixing of the hot and cold portions of catalyst in the regenerator can also be advantageous, e.g., to prevent undesirable localized catalyst hydrothermal deactivation.

The catalyst regeneration systems and processes of the present invention are particularly well-suited for the regeneration of heavily coked catalyst particles derived from OTO reaction systems and, more specifically, can allow for regenerating heavily coked catalyst particles while controlling the temperature of the regeneration process.

In one embodiment, the catalyst regeneration process can comprise a step of contacting a portion of the spent catalyst in the regenerator (the regenerator having a catalyst bed height ($H_c$), a catalyst cooler inlet height ($H_i$), and an catalyst cooler outlet height ($H_o$)) with an oxygen-containing regeneration medium at a first temperature, and/or otherwise under conditions effective, to at least partially regenerate the spent catalyst, and a step of conducting a portion of the catalyst from the regenerator to a catalyst cooler to form a cooled portion of the catalyst. This process can optionally result in many of the advantages described further herein.

A catalyst regeneration process useful in the present invention can include any process that efficiently removes at least a portion of the carbonaceous deposits from the coked catalyst composition to form a regenerated catalyst composition having increased catalytic activity over the coked catalyst composition. The catalyst can be regenerated in any number of conventional methods, such as batch, continuous, semi-continuous, or a combination thereof. Continuous catalyst regeneration is a preferred method. In an embodiment, the catalyst can be regenerated such that the level of coke remaining on the catalyst can be from about 0.01 wt % to about 15 wt %. In another embodiment, the level of coke remaining on the catalyst composition can be from about 0.01 to about 5 wt %, based on the total weight of the regenerated catalyst composition. In this particular embodiment, it is preferable that the catalyst to be regenerated has a level of coke of at least about 6 wt %, preferably from about 6 wt % to about 13 wt %, for example form about 6.5 wt % to about 10 wt %.

The catalyst regenerator of the present invention can include a regeneration zone and a separation zone. In the regeneration zone, the spent catalyst can contact the regeneration medium, preferably as a turbulent dense bed or phase, under conditions (e.g., at a temperature and pressure) effective to at least partially regenerate the spent catalyst. Specifically, the conditions are preferably effective to convert the spent catalyst and the regeneration medium to regenerated catalyst and gaseous byproducts of the regeneration process. The regenerated catalyst may be fully or partially regenerated. The gaseous byproducts, optionally with entrained catalyst and/or unreacted regeneration medium, can exit the dense phase and can form a dilute phase, which can extend from the surface of the dense phase to the top of the separation zone. The separation zone can be adapted to separate the entrained catalyst from the gaseous components in the dilute phase, and to return the entrained catalyst to the regeneration zone.

A majority of the catalyst regeneration can advantageously occur in a regeneration zone, the temperature of which can preferably be maintained from about 527° C. to about 760° C., and, in a related embodiment, from about 600° C. to about 732° C. Because the regeneration reaction typically takes place at a temperature significantly higher than the OTO conversion reaction in the reaction zone, e.g., about 93° C. to about 150° C. higher, it can often be desirable to cool at least a portion of the regenerated catalyst to a lower temperature before it is sent back to the reactor. One or more catalyst coolers, which can be located externally, internally, or both, to the catalyst regenerator, can be used to remove heat from the regenerated catalyst after it has been withdrawn from the catalyst regenerator.

The particular type of catalyst cooler implemented in the present invention may vary widely, and may not be critical, provided that adequate cooling of the catalyst can be attained. In an embodiment, the catalyst cooler comprises a shell and tube type heat exchanging device or a jacketed pipe heat exchange device. Included in the category of shell and tube type heat exchange devices are bayonet tube (tube-inside-tube) exchangers and U-tube exchangers.

Desirably, catalyst regeneration can be carried out after the spent catalyst has been stripped of most of the readily removable organic materials (organics), e.g., interstitial hydrocarbons, in a stripper or stripping chamber. This stripping can be achieved by passing a stripping medium, e.g., a stripping gas, over the spent catalyst at an elevated temperature. Gases suitable for stripping include steam, nitrogen, helium, argon, methane, $CO_2$, CO, hydrogen, and mixtures thereof. A preferred gas is steam. The gas hourly space velocity (GHSV) of the stripping gas, based on volume of gas to volume of catalyst and coke, is from about 0.1 $hr^{-1}$ to about 20,000 $hr^{-1}$. Acceptable temperatures of stripping are from about 250° C. to about 750° C., and desirably from about 400° C. to about 600° C. Acceptable stripping pressures are from about 5 psig (about 34 kPag) to about 50 psig (about 340 kPag), more preferably from about 10 psig (about 69 kPag) to about 30 psig (about 210 kPag), and most preferably from about 20 psig (about 140 kPag) to about 25 psig (about 170 kPag). The stripping pressure is largely dependent upon the pressure in the reactor (e.g., in the reaction zone) and in the catalyst regenerator.

The regenerator system can include one or more catalyst inlets for receiving spent catalyst from a reactor or reaction unit. The regenerator system can also include one or more catalyst cooler inlets for conducting the at least partially regenerated catalyst from the regenerator to the catalyst cooler. In one embodiment, the spent catalyst can be transported in a catalyst supply conduit (e.g., a tubular member) from the reactor or an intermediate vessel (e.g., a catalyst stripper) to the regenerator, e.g., for admixture with cold catalyst. A conduit can then direct the coked catalyst to the catalyst regenerator.

In an embodiment, the transport conduit preferably enters the regeneration zone of the catalyst regenerator and can release the coked catalyst into the regeneration zone for carbonaceous deposit removal. The transport conduit optionally includes a plurality of second ends for evenly distributing the spent catalyst in the regeneration zone. In one preferred embodiment, one or more of the plurality of second ends can extend into the regeneration zone, preferably longitudinally with respect to the catalyst regenerator, and can pass through a (laterally extending) distributor grid, through which the regeneration medium can advantageously be introduced into the regeneration zone. In this embodiment, the one or more of the plurality of second ends can release the spent catalyst composition into the regeneration zone at a position above the distributor grid.

The bulk of the regeneration process preferably occurs in the relatively dense phase of the regeneration zone. On a volume basis, the dense phase optionally comprises from about 2 vol % to about 45 vol %, preferably from about 20 vol % to about 35 vol %, of the regeneration zone, based on the total volume of the regeneration zone. On a weight basis, the dense phase preferably comprises from about 45 wt % to about 98 wt %, optionally from about 85 wt % to about 95 wt %, based on the total weight of the catalyst in the regeneration zone.

As used herein, longitudinal means extending in a direction perpendicular to grade (e.g., vertical), and lateral means extending in a direction parallel to grade (e.g., horizontal). Also as used herein, the proximal end of an object is the portion of the object that is nearest to grade, and the distal end of the object is the portion of the object that is furthest removed from grade.

In some embodiments, the regeneration zone also preferably includes one or more regeneration medium inlets for receiving a regeneration medium, preferably air, molecular oxygen, or a mixture thereof. The regeneration medium conduits can carry the regeneration medium from a regeneration medium source, such as a pressurized regeneration medium containment vessel in which the regeneration medium is stored, to the one or more regeneration medium inlets. In one embodiment, at least one nozzle introduces the regeneration medium into the regeneration zone. Preferably, the regeneration medium is introduced into the catalyst regenerator at a rate of about 50 to about 500 standard cubic feet (scf)/lb coke burned (about 3.1 to about 31.2 standard cubic meters (scm)/kg coke burned), more preferably about 150 to about 400 scf/lb coke burned (about 9.4 to about 25.0 scm/kg coke burned), and even more preferably about 200 to about 350 scf/lb coke burned (about 12.5 to about 21.9 scm/kg coke burned).

Preferably, the coked catalyst is communicated to the regenerator through a transport conduit, e.g., a pipe or tubing. The lateral cross-sectional area of the transport conduit may vary, but preferably is less than the lateral cross-sectional area of the regeneration zone, although, in an alternate embodiment, it could also be greater.

Preferably, the oxygen-containing regeneration medium can be added directly into the regeneration zone, rather than in the transport conduit that communicates the coked catalyst from the reactor to the regeneration zone. Desirably, the regeneration medium, preferably a gas, comprises molecular oxygen or other oxidants. Examples of oxidants suitable in the regeneration medium can include, but are not necessarily limited to, $O_2$, $O_3$, $SO_3$, $N_2O$, $NO$, $NO_2$, $N_2O_5$, and mixtures thereof. Air, alone or diluted with nitrogen or $CO_2$, are particularly desirable regeneration media. The oxygen concentration in air can be altered (e.g., reduced) to a controlled level, e.g., to minimize overheating of, or creating hot spots in, the catalyst regenerator. The catalyst can also be regenerated reductively with hydrogen, mixtures of hydrogen and carbon monoxide, or other suitable reducing gases.

In one embodiment, the catalyst cooler has an entrance standpipe. To increase the catalyst circulation rate between the regenerator and the catalyst cooler, the entrance standpipe can preferably be cylindrical in shape and can preferably be of substantially constant diameter. This preferred arrangement can allow for less restricted flow between the regenerator and the catalyst cooler.

Figure 2:
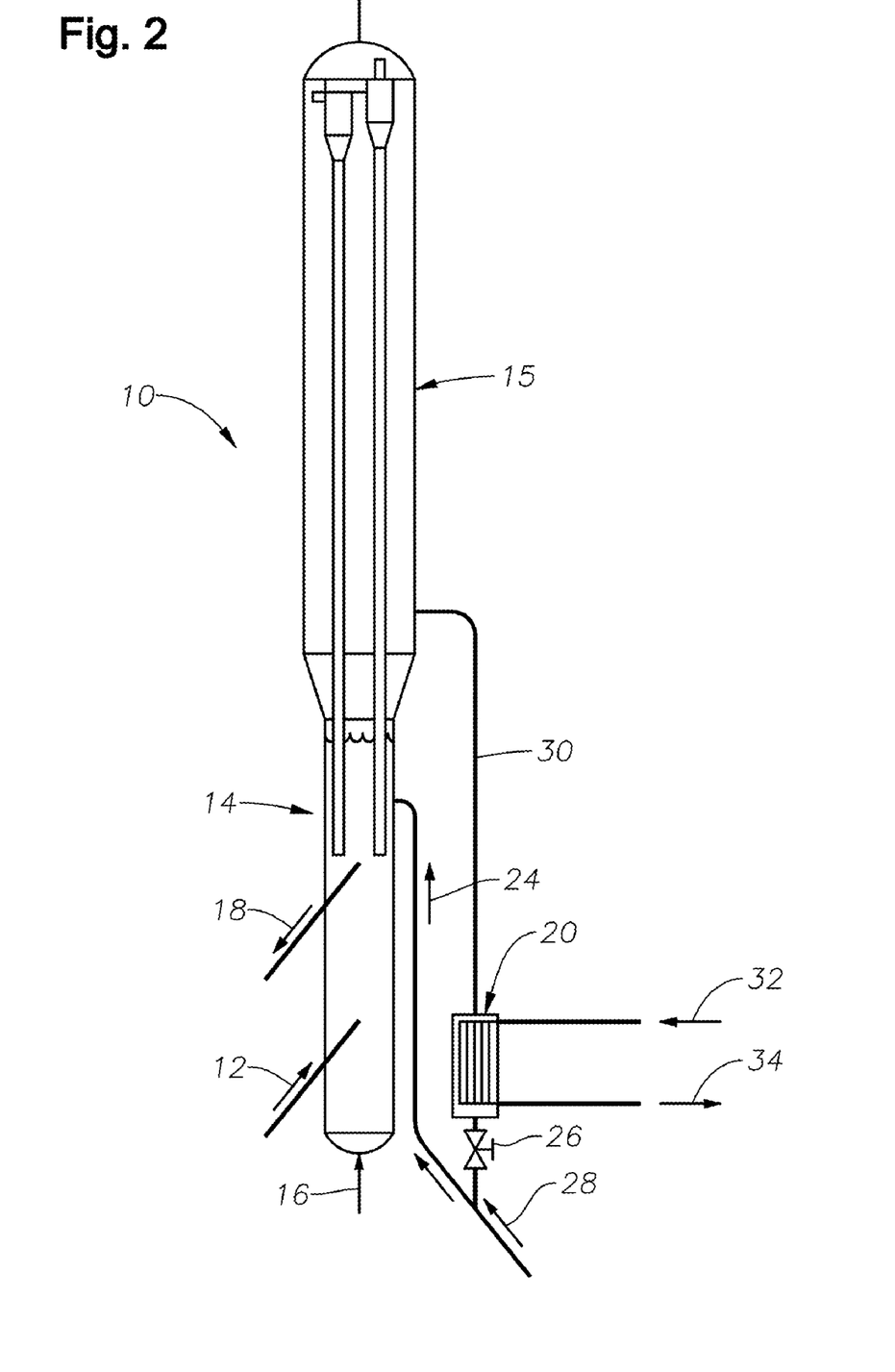
FIG. 2 illustrates an embodiment of the circulation scheme between the regenerator and external catalyst cooler in a methanol to olefins regenerator system.

In one embodiment of the invention, the regenerator has one or more catalyst cooler inlets and one or more catalyst cooler outlets, with at least one of the catalyst cooler outlets being preferably located above at least one of the catalyst cooler inlets, while still being within the catalyst bed of the regenerator (see FIG. 2). In another embodiment, at least one of the catalyst outlets is located above the catalyst bed of the reactor, e.g., in the separation zone of the regenerator (See FIG. 3), also referred to herein as the "dilute phase." In the regenerator, the larger solid particles, which can be projected above the bed by eruption of gas bubbles through the catalyst bed surface or which can be entrained in the gas stream, typically fall (back) into the fluidized bed. This arrangement can advantageously result in a more even distribution of the entrained cooled catalyst into the bed (e.g., through the cyclone diplegs) or by non-entrained cooled catalyst falling to the bed, thus causing relatively thorough mixing of the catalyst.

In yet another embodiment, at least one of the catalyst cooler outlets conducts catalyst from the catalyst cooler into the regenerator at a substantially perpendicular angle, relative to the regenerator. This positioning of the at least one of the catalyst cooler outlets facilitates radial mixing, which can lead to reduction/minimization of undesirable catalyst hot spots and cold spots.

In one embodiment, the process further comprises the step of conducting the catalyst through a conduit and a lift air nozzle before entering the regenerator, the lift air nozzle having a diameter so as not be so big as to block catalyst flow all by itself. The lift air nozzle diameter is preferably sized to provide about 10-20 ft/sec (about 3-6.1 m/sec) gas flow in the lift line, and there should preferably be enough annular space around the nozzle for a catalyst flux of less than about 100 $lb/ft^2 \cdot sec$ (less than about 500 $kg/m^2 \cdot sec$). In another embodiment, the lift air nozzle is downstream of the regenerator catalyst inlet.

In one embodiment, the process further comprises the step of measuring the catalyst $\Delta T$ between the at least one catalyst cooler inlet and the corresponding catalyst cooler outlet. In one embodiment, the catalyst $\Delta T$ can be from above 0° C. to about 350° C., for example from above 0° C. to about 300° C., from above 0° C. to about 200° C., or from above 0° C. to about 150° C. In another embodiment, the catalyst $\Delta T$ can be from about 10° C. to about 350° C., for example from about 25° C. to about 300° C., from about 50° C. to about 200° C., from about 100° C. to about 250° C., from about 5° C. to about 125° C., or from about 10° C. to about 175° C.

Compared to prior art processes, the process of the present invention can also advantageously result in a reduction in the catalyst hold-up, thereby reducing the total amount of catalyst required in the system, as well as reducing the time in which the catalyst is exposed to deactivating conditions in the regenerator. As used herein, "catalyst hold-up" means the amount of catalyst (usually measured in mass) within a section of the equipment, or sometimes within all the reaction system's equipment summed together. Typically, when mass is measured, catalyst hold-up understandably increases with increasing catalyst coke loading. The catalyst hold-up in the regenerator bed can alternately be measured by determining the pressure difference ($\Delta P$) between the bottom of the regenerator and the dilute phase located above the bed. The catalyst weight hold-up can be determined from the $\Delta P$ and cross sectional area, and this, in combination with a catalyst bed density (calculable from an internal bed $\Delta P$ across a known length), can then be used to calculate the catalyst bed height.

In one embodiment, the catalyst hold-up in the regenerator configurations according to the invention can be decreased by at least 20%, more preferably at least 25%, and most preferably at least 30%, compared to the catalyst hold-up in a regenerator configuration with a single external catalyst cooler having only one cooler inlet and only one cooler outlet.

In another embodiment, the process further comprises the step of making a polyolefin product comprising polymerizing the light olefin product to make a polyolefin product.

In some embodiments, during regeneration, the regenerator can produce a steady state afterburn of 200° C. or less, and optionally a steady state CO concentration in the regenerator flue gas of 10,000 ppmv (i.e., parts per million by volume) or less. Preferably, the afterburn can be 100° C. or less. Preferably, the CO concentration in the regenerator flue gas can be 1000 ppmv or less. In some embodiments, it may be necessary to promote oxidation of carbon monoxide to carbon dioxide under catalyst regeneration conditions, in order to decrease the incidence of afterburn. U.S. Patent Application Publication No. 2003/0163010 discloses metals useful in the present invention for promoting oxidation of carbon monoxide to carbon dioxide, while catalyst regeneration conditions can include those described, e.g., in U.S. Pat. Nos. 4,072,600 and 4,350,614, the entire contents of each of which being incorporated herein by reference. Such metals can be oxidation promoters such as platinum, palladium, iridium, osmium, rhodium, ruthenium, rhenium, and combinations thereof. The catalyst composition may contain, for example, from about 0.01 ppmw to about 100 ppmw (parts per million by weight) oxidation promoter, usually from about 0.01 ppmw to about 50 ppmw or from about 0.01 ppmw to about 5 ppmw.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition can be added to the regenerator containing a regeneration medium of oxygen and water, as described in U.S. Pat. No. 6,245,703, which is herein fully incorporated by reference.

Additionally or alternately, the present invention can include one or more of the following embodiments as follows.

Embodiment 1

A method for controlling regenerator temperature in an oxygenates-to-olefins system, comprising the steps of: (a) contacting a feed comprising an oxygenate with a catalytically effective amount of a molecular sieve-containing catalyst in a reaction zone under conditions sufficient to convert said oxygenate to a product containing light olefins, and thereby forming an at least partially coked catalyst; (b) conducting a portion of the at least partially coked catalyst from the reaction zone to a regenerator having a catalyst bed, a catalyst cooler, a catalyst cooler inlet, a catalyst cooler outlet, a catalyst bed height ($H_c$), an catalyst cooler inlet height ($H_i$), and a catalyst cooler outlet height ($H_o$); (c) contacting a portion of the at least partially coked catalyst in the regenerator with an oxygen-containing regeneration medium at a first temperature, under conditions effective to at least partially regenerate the at least partially coked catalyst; and (d) conducting a portion of the catalyst from the regenerator through the catalyst cooler inlet to the catalyst cooler to form a cooled portion of catalyst, which is then conducted through the catalyst cooler outlet back into the regenerator to control temperature in the regenerator, wherein $H_o$ is preferably greater than $H_i$.

Embodiment 2

The method of embodiment 1, wherein the regenerator comprises a regeneration zone and a separation zone.

Embodiment 3

The method of any of the previous embodiments, wherein the catalyst cooler outlet is located such that $H_o$ is greater than $H_c$.

Embodiment 4

The method of any of the previous embodiments, wherein the regenerator has a regenerator height ($H_r$), at least two catalyst cooler inlets, and at least two catalyst cooler outlets, and wherein: (i) each inlet and outlet has a center; (ii) two or more of the at least two outlet centers and the at least two cooler inlet centers define a line; (iii) two or more of the at least two cooler inlet centers and the regenerator height form one or more inlet planes; (iv) two or more of the at least two cooler outlet centers and the regenerator height define one or more outlet planes; and (v) at least one of the one or more inlet planes and at least one of the one or more outlet planes are substantially not coplanar.

Embodiment 5

The method of embodiment 4, further comprising recirculating catalyst from the catalyst cooler through the at least two cooler outlets into the regenerator, wherein the at least two cooler inlets are positioned at first positions along the regenerator height at the common inlet height ($H_i$), the at least two cooler outlets are positioned at second positions along the regenerator height at the common outlet height ($H_o$), and the at least two first positions are below the at least two second positions such that $H_o$ is preferably greater than $H_i$.

Embodiment 6

A method for controlling regenerator temperature in an oxygenates-to-olefins system, comprising the steps of: (a) contacting a feed comprising an oxygenate with a catalytically effective amount of a molecular sieve-containing catalyst in a reaction zone under conditions sufficient to convert said oxygenate to a product containing light olefins, and thereby forming an at least partially coked catalyst; (b) conducting a portion of the at least partially coked catalyst from the reaction zone to a regenerator having a regenerator height ($H_r$), a catalyst bed, a catalyst bed height ($H_c$), at least two catalyst cooler inlets, and at least two catalyst cooler outlets; (c) contacting a portion of the at least partially coked catalyst in the regenerator with an oxygen-containing regeneration medium at a first temperature, under conditions effective to at least partially regenerate the at least partially coked catalyst; and (d) conducting a portion of the catalyst from the regenerator through one or more of the at least two catalyst cooler inlets to the catalyst cooler to form a cooled portion of catalyst, which is then conducted through one or more of the at least two catalyst cooler outlets back into the regenerator to control temperature in the regenerator, wherein: (i) each inlet and outlet has a center; (ii) two or more of the at least two outlet centers and the at least two cooler inlet centers define a line; (iii) two or more of the at least two cooler inlet centers and the regenerator height form one or more inlet planes; (iv) two or more of the at least two cooler outlet centers and the regenerator height define one or more outlet planes; and (v) at least one of the one or more inlet planes and at least one of the one or more outlet planes are substantially not coplanar.

Embodiment 7

The method of embodiment 6, wherein the at least two cooler inlets are positioned at first positions along the regenerator height at a common inlet height ($H_i$), the at least two cooler outlets are positioned at second positions along the regenerator height at a common outlet height ($H_o$), and the at least two first positions are above the at least two second positions such that $H_i$ is greater than $H_o$.

Embodiment 8

The method of any of the previous embodiments, wherein the regenerator further comprises at least one circulation inlet and at least one circulation outlet in fluid communication with the at least one circulation inlet to form at least one circulation loop that does not encompass a catalyst cooler therewithin.

Embodiment 9

The method of any of the previous embodiments, wherein the catalyst cooler outlet conducts catalyst into the regenerator at a substantially perpendicular angle, relative to the regenerator.

Embodiment 10

The method of any of the previous embodiments, wherein the catalyst cooler has an entrance standpipe, which is cylindrical in shape and of substantially constant diameter.

Embodiment 11

The method of any of the previous embodiments, further comprising the step of conducting the catalyst through a conduit and a lift air nozzle before entering the regenerator.

Embodiment 12

The method of embodiment 11, wherein the lift air nozzle is downstream of the catalyst return line inlet.

Embodiment 13

The method of any of the previous embodiments, further comprising the step of measuring a catalyst $\Delta T$, which is a temperature at the catalyst cooler inlet minus a temperature at the catalyst cooler outlet, and wherein the catalyst $\Delta T$ is about 0° C. to about 350° C.

Embodiment 14

A method of making an olefin product from an oxygenate-containing feed comprising performing the method according to any of the previous embodiments, and further comprising the steps of: (e) conducting at least a portion of the catalyst from the regenerator back to the reaction zone; and (f) isolating and optionally purifying the product containing light olefins.

Embodiment 15

A method of making a polyolefin product comprising contacting the light olefin product produced according to the method of embodiment 14, optionally along with one or more polymerizable comonomers, with an initiator, in the presence of a catalyst, or both, under conditions sufficient to form a polyolefin product.

EXAMPLES

Example 1

Figure 1:
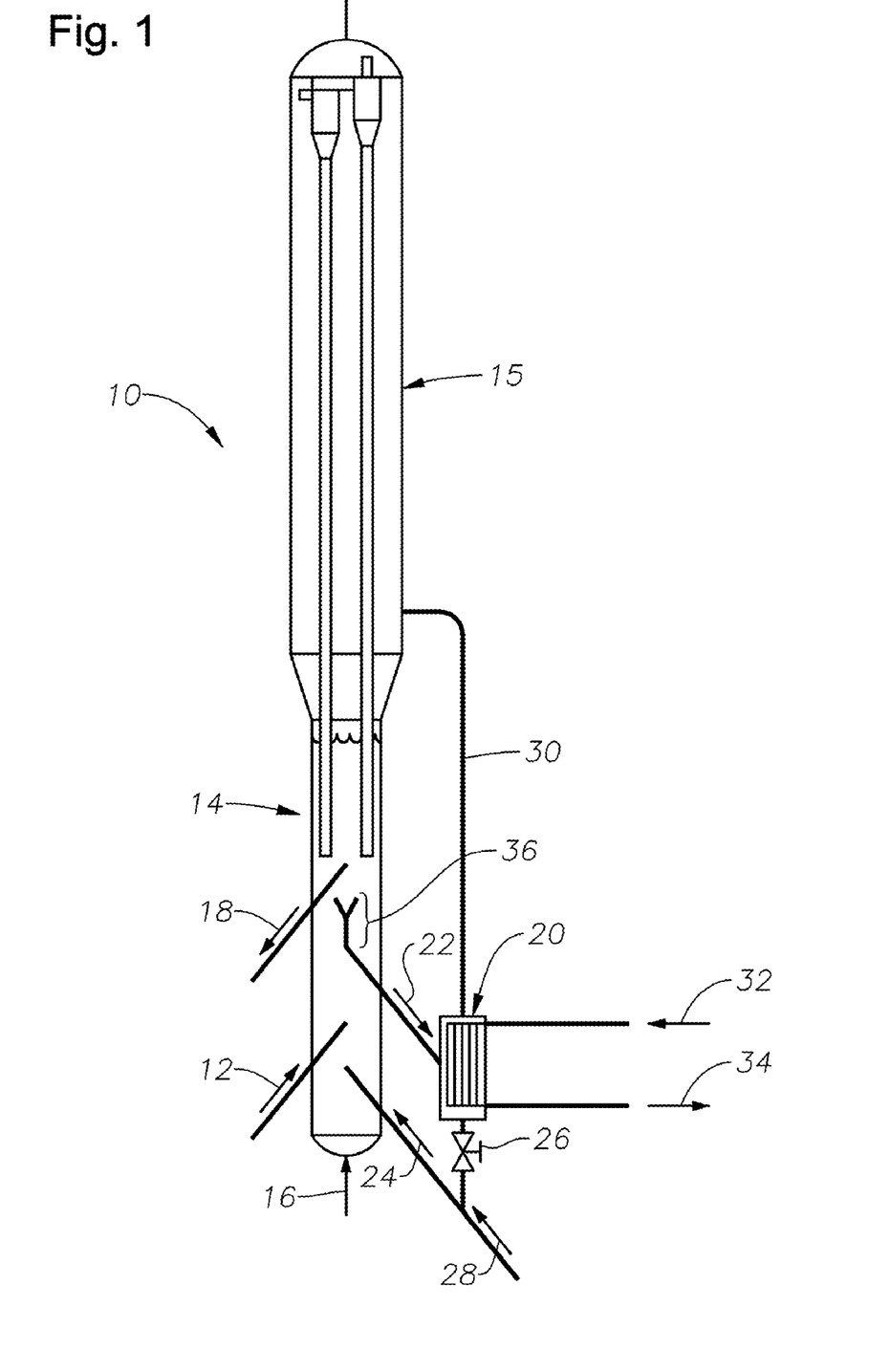
FIG. 1 illustrates a side view of an existing regenerator and catalyst cooler configuration and the circulation scheme between the regenerator and external catalyst cooler in a methanol to olefins regenerator system.

The regenerator and catalyst cooler system utilized in this example is shown in FIG. 1 and described as follows. Product from the OTO reactor (not shown), as described hereinabove (typically a slip stream, e.g., representing less than 25 wt % of the total catalyst weight in the reactor/regenerator system, for example less than 20 wt %, less than 15 wt %, or not more than 10 wt %), enters the regenerator vessel (10) through a line (12), the vessel (10) containing a bed of MTO catalyst (14) and an oxygen-containing regeneration medium inlet (16). At least a portion of the at least partially regenerated catalyst then enters a first conduit (22) means for conducting MTO catalyst from the regenerator vessel (10) to the catalyst cooler (20) containing a catalyst cooler medium, such as steam/water, which enters relatively cool (through line 32) and exits relatively heated (through line 34), thus cooling the catalyst flowing through the catalyst cooler (20). Upon actuation of a slide valve (26), the catalyst, preferably assisted in fluidization by a fluidization medium, such as air or nitrogen (from line 28), then enters and a second conduit means (24) for conducting cooled MTO catalyst from the catalyst cooler (20) to the regenerator vessel (10), typically to the catalyst bed (14). At least a portion of the regenerated and/or cooled catalyst in the catalyst bed (14) is then sent back to the OTO reactor. Cooler vent line (30) optionally allows for venting of volatile components, such as gases, from the catalyst cooler (20) to the regenerator (10), typically to the dilute phase of the regenerator (15) above the catalyst bed (14).

Example 2

In this particular example, the regenerator and catalyst cooler system would be similar to that of Example 1, with the exception that the following changes were made (see FIG. 2):
  a. the internal catalyst collection cone, line, and elbow (collectively 36) on the catalyst cooler inlet (22) were removed in favor of an opening in the catalyst bed wall connected to the catalyst bed (14);
  b. the location of the catalyst return line (24) from the catalyst cooler (20) was changed from being near the bottom of the regenerator catalyst bed (14) to near the top of the catalyst bed (14); and
  c. the angle of the regenerator catalyst inlet entrance (24) was also changed from at least about 45° past the horizontal (typically as much as approximately vertical, in the direction counter to regenerator flow) to approximately horizontal.

Other modifications between the regenerator and catalyst cooler system of Example 1 and of Example 2 can additionally or alternately include one or more of the following:
  d. the catalyst cooler inlet (22) for the catalyst cooler (20) can have a substantially constant diameter; and/or
  e. a lift air nozzle (not shown) having a relatively smaller diameter can be used in the catalyst return line (24) and/or in the fluidization supply line (28).

Example 3

Figure 3:
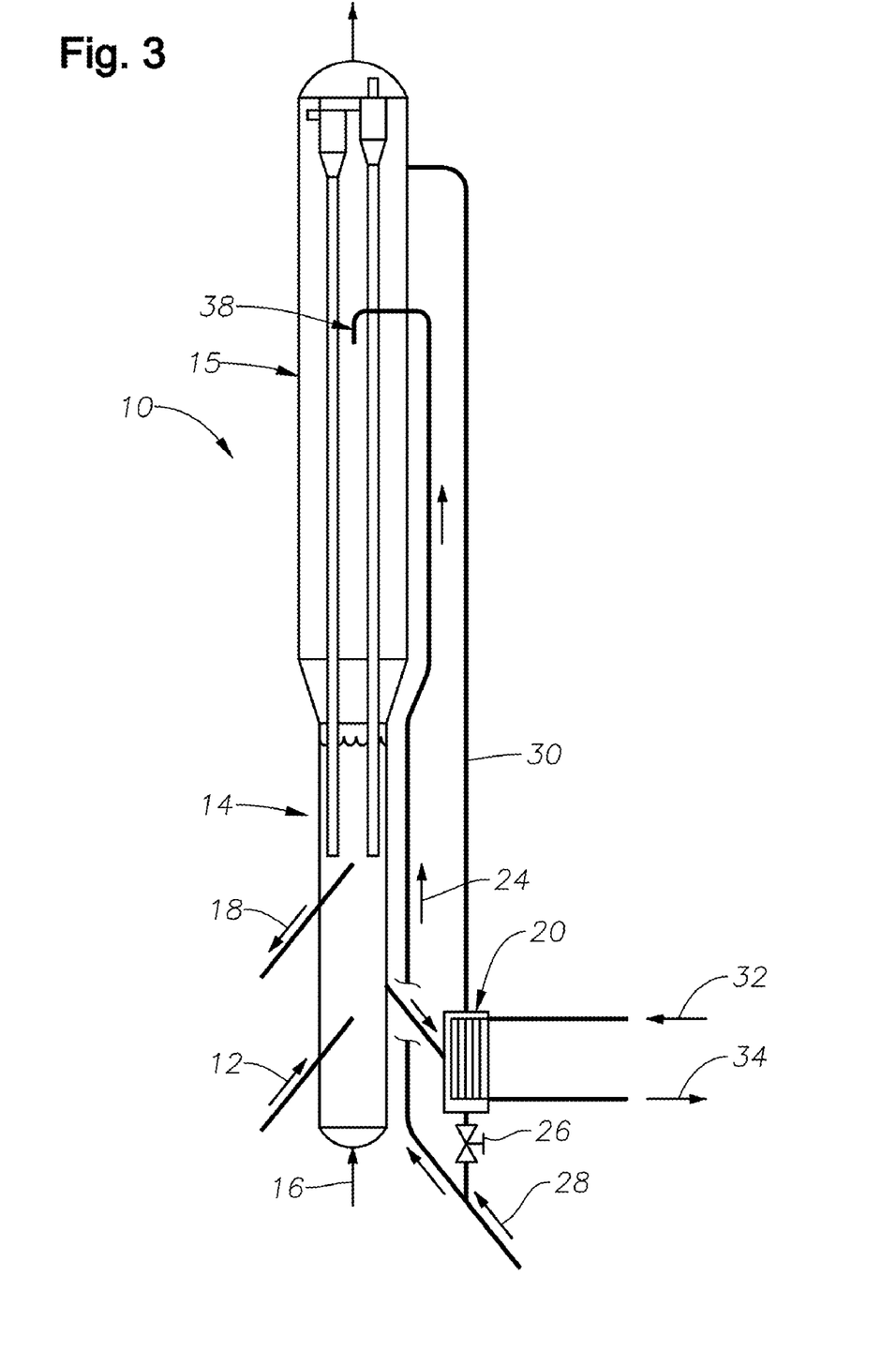
FIG. 3 illustrates a side view of an embodiment of the circulation scheme between the regenerator and external catalyst cooler in a methanol to olefins regenerator system where the cooled catalyst is returned to the regenerator at a height higher than that of the embodiment of FIG. 2.

In this particular example, the regenerator and catalyst cooler system are similar to that of Example 2, with the exception that the catalyst cooler return line (24) is moved so that the catalyst re-enters the regenerator (10) in the location of the dilute phase (15) outside of the catalyst bed (14), as shown in FIG. 3. Optionally, the catalyst cooler return line (24) introduces the cooled catalyst into the dilute phase (15) of the regenerator (10) in an approximately vertical orientation in the direction of the regenerator flow; also optionally, this concurrent flow of cooled catalyst can be disrupted by one or more baffles (e.g., such as 38) disposed within the dilute phase (15) of the regenerator (10).

Examples 4-8

Figure 4:
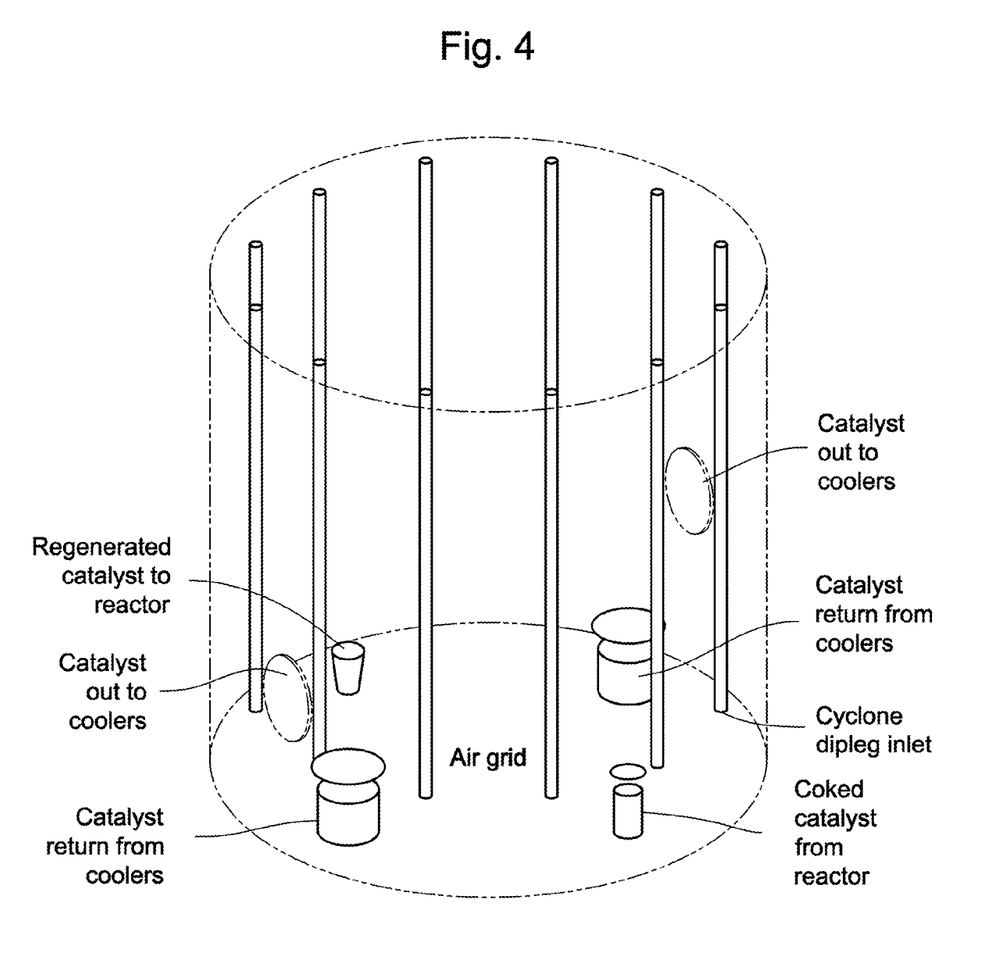
FIG. 4 illustrates a perspective view of an embodiment of the design of a regenerator system according to the invention.
Figure 5A:
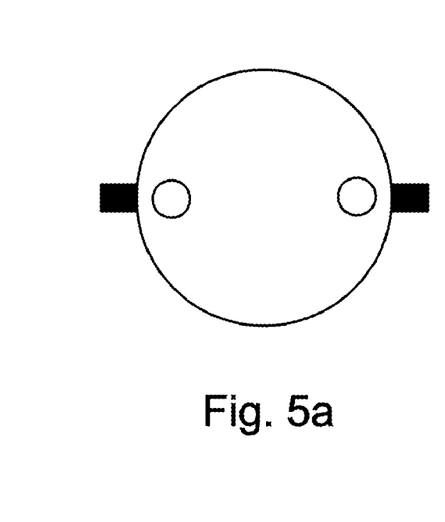
Figure 5B:
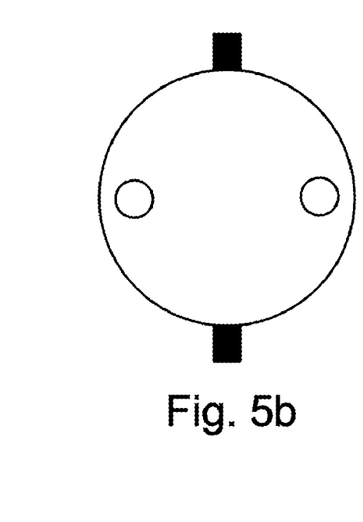
Figure 5C:
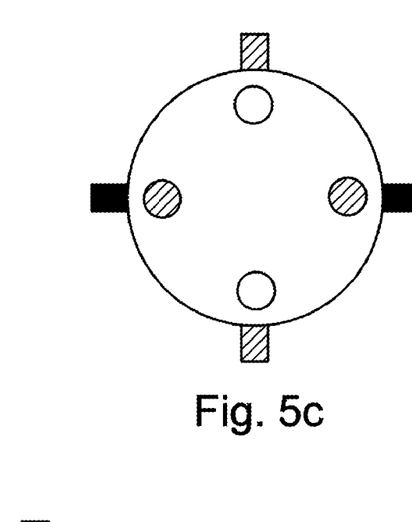
Figure 5D:
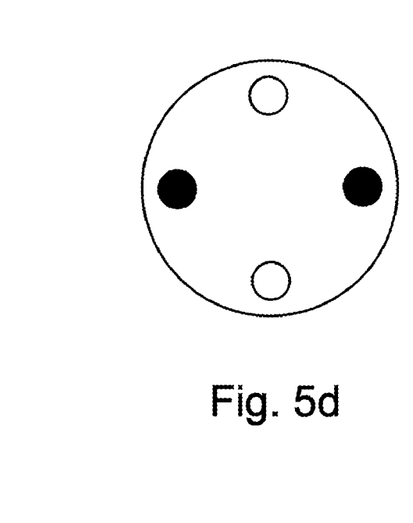
Figure 5E:
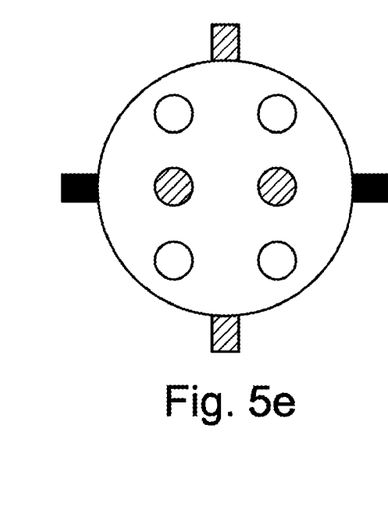

Examples 4-8 represent the central regenerator/catalyst cooler configurations of FIGS. 5a-5e, respectively, with FIG. 5a and FIG. 4 (Example 4) being oriented in a similar configuration with respect to the catalyst cooler inlets and outlets. In one embodiment, these configurations of Examples 4-8 can be used in tandem with one or more of the systems described in Examples 1-3. Although the representations in FIGS. 5a-5e show only cross-sections and relative orientations in the plane of the paper, it is preferable that one or more (more preferably most or all) of the circular geometries are offset from one or more (more preferably most or all) of the rectangular geometries out of the plane of the paper, as shown in FIG. 4 for the configuration in FIG. 5*a*. Nevertheless, the relative orientations of one or more of the inlets and outlets in FIGS. 5*a*-5*e* may alternately (but less preferably) be substantially coplanar within the plane of the paper.

Based on some computational fluid dynamics (CFD) simulations, each of Examples 4-8 indicated superior catalyst cooling results, as compared with configurations having only one catalyst cooler inlet and one catalyst cooler outlet. Further, based on the CFD simulations, Examples 5-8, in which the catalyst cooler inlets are offset from the catalyst cooler outlets in the plane of the paper (in Examples 5-7, this offset is set at approximately 90°), showed superior catalyst cooling results, as compared with the configuration of Example 4, in which the catalyst cooler inlets are offset in the plane perpendicular to the paper but are not offset in the plane of the paper.

While the present invention has been described and illustrated by reference to particular embodiments, those of ordinary skill in the art will appreciate that the invention lends itself to variations not necessarily illustrated herein. For example, additionally contemplated molecular sieve catalyst compositions can include one or more other molecular sieves in combination. For this reason, then, reference should be made solely to the appended claims for purposes of determining the true scope of the present invention.

What is claimed is:

1. A method for controlling regenerator temperature in an oxygenates-to-olefins system, comprising the steps of:
    a. contacting a feed comprising an oxygenate with a catalytically effective amount of a molecular sieve-containing catalyst in a reaction zone under conditions sufficient to convert said oxygenate to a product containing light olefins, and thereby forming an at least partially coked catalyst;
    b. conducting a portion of the at least partially coked catalyst from the reaction zone to a regenerator having a catalyst bed, a catalyst cooler, a catalyst cooler inlet, a catalyst cooler outlet, a catalyst bed height ($H_c$), an catalyst cooler inlet height ($H_i$), and a catalyst cooler outlet height ($H_o$);
    c. contacting a portion of the at least partially coked catalyst in the regenerator with an oxygen-containing regeneration medium at a first temperature, under conditions effective to at least partially regenerate the at least partially coked catalyst; and
    d. conducting a portion of the catalyst from the regenerator through the catalyst cooler inlet to the catalyst cooler to form a cooled portion of catalyst, which is then conducted through the catalyst cooler outlet back into the dilute phase of the regenerator to control temperature in the regenerator,
wherein $H_o$ is greater than $H_i$.

2. The method of claim 1, wherein the regenerator comprises a regeneration zone and a separation zone.

3. The method of claim 1, wherein the catalyst cooler outlet is located such that $H_o$ is greater than $H_c$.

4. The method of claim 1, wherein the regenerator has a regenerator height ($H_r$), at least two catalyst cooler inlets, and at least two catalyst cooler outlets, and wherein:
    (i) each inlet and outlet has a center;
    (ii) two or more of the at least two outlet centers and the at least two cooler inlet centers define a line;
    (iii) two or more of the at least two cooler inlet centers and the regenerator height form one or more inlet planes;
    (iv) two or more of the at least two cooler outlet centers and the regenerator height define one or more outlet planes; and
    (v) at least one of the one or more inlet planes and at least one of the one or more outlet planes are substantially not coplanar.

5. The method of claim 4, wherein the at least two cooler inlets are positioned at first positions along the regenerator height at the common inlet height ($H_i$), the at least two cooler outlets are positioned at second positions along the regenerator height at the common outlet height ($H_o$), and the at least two first positions are below the at least two second positions such that $H_o$ is greater than $H_i$.

6. The method of claim 4, wherein the regenerator further comprises at least one circulation inlet and at least one circulation outlet in fluid communication with the at least one circulation inlet to form at least one circulation loop that does not encompass a catalyst cooler therewithin.

7. The method of claim 1, wherein the regenerator further comprises at least one circulation inlet and at least one circulation outlet in fluid communication with the at least one circulation inlet to form at least one circulation loop that does not encompass a catalyst cooler therewithin.

8. The method of claim 1, wherein the catalyst cooler outlet conducts catalyst into the regenerator at a substantially perpendicular angle, relative to the regenerator.

9. The method of claim 1, wherein the catalyst cooler has an entrance standpipe, which is cylindrical in shape and of substantially constant diameter.

10. The method of claim 1, further comprising the step of conducting the catalyst through a conduit and a lift air nozzle before entering the regenerator.

11. The method of claim 10, wherein the lift air nozzle is downstream of the catalyst return line inlet.

12. The method of claim 1, further comprising the step of measuring a catalyst $\Delta T$, which is a temperature at the catalyst cooler inlet minus a temperature at the catalyst cooler outlet, and wherein the catalyst $\Delta T$ is above 0° C. to about 350° C.

13. A method of making an olefin product from an oxygenate-containing feed comprising performing the method according to claim 1, and further comprising the steps of:
    e. conducting at least a portion of the catalyst from the regenerator back to the reaction zone; and
    f. isolating and optionally purifying the product containing light olefins.

14. A method of making a polyolefin product comprising contacting the light olefin product produced according to the method of claim 13, optionally along with one or more polymerizable comonomers, with an initiator, in the presence of a catalyst, or both, under conditions sufficient to form a polyolefin product.

15. A method for controlling regenerator temperature in an oxygenates-to-olefins system, comprising the steps of:
    a. contacting a feed comprising an oxygenate with a catalytically effective amount of a molecular sieve-containing catalyst in a reaction zone under conditions sufficient to convert said oxygenate to a product containing light olefins, and thereby forming an at least partially coked catalyst;
    b. conducting a portion of the at least partially coked catalyst from the reaction zone to a regenerator having a regenerator height ($H_r$), a catalyst bed, a catalyst bed height ($H_c$), at least two catalyst cooler inlets, and at least two catalyst cooler outlets;

c. contacting a portion of the at least partially coked catalyst in the regenerator with an oxygen-containing regeneration medium at a first temperature, under conditions effective to at least partially regenerate the at least partially coked catalyst; and d. conducting a portion of the catalyst from the regenerator through one or more of the at least two catalyst cooler inlets to the catalyst cooler to form a cooled portion of catalyst, which is then conducted through one or more of the at least two catalyst cooler outlets back into the regenerator to control temperature in the regenerator and the catalyst hold-up in the regenerator configurations according to the invention is decreased by at least 30% compared to the catalyst hold-up in a regenerator configuration with a single external catalyst cooler having only one cooler inlet and only one cooler outlet, wherein:
(i) each inlet and outlet has a center;
(ii) two or more of the at least two outlet centers and the at least two cooler inlet centers define a line;
(iii) two or more of the at least two cooler inlet centers and the regenerator height form one or more inlet planes;
(iv) two or more of the at least two cooler outlet centers and the regenerator height define one or more outlet planes; and
(v) at least one of the one or more inlet planes and at least one of the one or more outlet planes are substantially not coplanar.

16. The method of claim 15, wherein the at least two cooler inlets are positioned at first positions along the regenerator height at a common inlet height ($H_i$), the at least two cooler outlets are positioned at second positions along the regenerator height at a common outlet height ($H_o$).

17. The method of claim 16, wherein the regenerator further comprises at least one circulation inlet and at least one circulation outlet in fluid communication with the at least one circulation inlet to form at least one circulation loop that does not encompass a catalyst cooler therewithin.

18. The method of claim 15, wherein the regenerator further comprises at least one circulation inlet and at least one circulation outlet in fluid communication with the at least one circulation inlet to form at least one circulation loop that does not encompass a catalyst cooler therewithin.

19. A method of making an olefin product from an oxygenate-containing feed comprising performing the method according to claim 15, and further comprising the steps of:
g. conducting at least a portion of the catalyst from the regenerator back to the reaction zone; and
h. isolating and optionally purifying the product containing light olefins.

20. A method of making a polyolefin product comprising contacting the light olefin product produced according to the method of claim 19, optionally along with one or more polymerizable comonomers, with an initiator, in the presence of a catalyst, or both, under conditions sufficient to form a polyolefin product.

* * * * *